United States Patent
Burty et al.

(10) Patent No.: US 7,942,950 B2
(45) Date of Patent: May 17, 2011

(54) METHOD FOR CONTROLLING A MOLTEN METAL BATH BUBBLING IN A METALLURGICAL VESSEL AND A DEVICE FOR CARRYING OUT SAID METHOD

(75) Inventors: Marc Burty, Metz (FR); Charles Pusse, Kedange sur Canner (FR); Patrick Wetta, Saint Cyr sur Rhone (FR); Francis Sulin, Villeurbanne (FR); Claude Bertoletti, Marly (FR); Yves Borneque, Veckring (FR); Daniel Pernet, Marly (FR); Eric Carioli, Wallon Cappel (FR)

(73) Assignee: ArcelorMittal France, Saint Denis (FR)

( * ) Notice: Subject to any disclaimer, the term of this patent is extended or adjusted under 35 U.S.C. 154(b) by 94 days.

(21) Appl. No.: 11/630,988

(22) PCT Filed: Jun. 14, 2005

(86) PCT No.: PCT/FR2005/001460
§ 371 (c)(1),
(2), (4) Date: Apr. 17, 2007

(87) PCT Pub. No.: WO2006/013239
PCT Pub. Date: Feb. 9, 2006

(65) Prior Publication Data
US 2008/0047396 A1 Feb. 28, 2008

(30) Foreign Application Priority Data
Jul. 2, 2004 (FR) .................................. 04 07455

(51) Int. Cl.
*C21C 5/34* (2006.01)
*C21B 7/24* (2006.01)

(52) U.S. Cl. ............................................ 75/375; 266/81
(58) Field of Classification Search ................... 75/375; 266/81
See application file for complete search history.

(56) References Cited

U.S. PATENT DOCUMENTS
| | | | |
|---|---|---|---|
| 5,477,730 A | 12/1995 | Carter | |
| 5,633,462 A * | 5/1997 | Heaslip et al. | 73/649 |
| 6,264,716 B1 | 7/2001 | Kemeny et al. | |
| 7,254,433 B2 * | 8/2007 | Diab et al. | 600/336 |

FOREIGN PATENT DOCUMENTS
| | | |
|---|---|---|
| BE | 1 008 090 | 1/1996 |
| GB | 2 171 198 | 8/1986 |
| WO | 2004/017038 | 2/2004 |

* cited by examiner

*Primary Examiner* — Roy King
*Assistant Examiner* — Jie Yang
(74) *Attorney, Agent, or Firm* — Oblon, Spivak, McClelland, Maier & Neustadt, L.L.P.

(57) ABSTRACT

A method introducing a stirring gas through a vessel bottom, receiving a measurable mechanical vibration by at least one sensor fixed to the vessel or to a supporting frame thereof, filtering the thus detected vibration signals by a high pass filter and preferably by a low pass filter, sampling and digitizing the vibration signals for exposing them to a second filtering which is digital and calibrated upon the vessel vibration responses, sequencing the response, exposing each sequence to the calculation of a temporal moving mean square, and extracting the total effective value RMS (Root Mean Square) of the measured vibration signal therefrom. The effective value is used for controlling the stirring gas flowrate supplied to the vessel. The method can be used for a stirring stand of steel making shop ladles, converters, RH processes, electric arc furnaces, etc.

8 Claims, 2 Drawing Sheets

METHOD FOR CONTROLLING A MOLTEN METAL BATH BUBBLING IN A METALLURGICAL VESSEL AND A DEVICE FOR CARRYING OUT SAID METHOD

The invention relates to the bubbling in a metallurgical ladle, for steelworks in particular, by blowing of a stirring gas through the bottom. More generally, the invention relates to the bubbling of a bath of molten metal in any metallurgical vessel equipped accordingly, such as a steelworks converter, an arc furnace or an RH vessel for example, it being recalled nevertheless that bubbling is most commonly carried out nowadays at the in-ladle treatment stand.

It is known that treatment in a steelworks ladle (this preferential application will be taken as example hereinafter) makes it possible to perform various metallurgical operations, such as grading, deoxidation, denitriding or decarburation of the steel in the liquid state. The residence time of the metal in the ladle necessarily being limited for productivity reasons, the steel is ordinarily stirred to assist these various operations, which conventionally additionally involve an active slag floating on the surface.

Thus, when it is suitably conducted, ladle stirring enables the grade to be made homogeneous at the same time as it enables the metal-slag exchanges to be accelerated so as to more rapidly approach the thermodynamic equilibrium between these two phases. It thus favors metallurgical operations such as degassing or decarburation by continuously supplying "fresh" liquid steel to the upper layer in reactive contact with the slag. It also assists the decantation of inclusions and therefore participates in the final inclusion cleanliness of the cast steel. It will thus be understood that there may be different optimal stirring intensities depending on the metallurgical operation considered, and such may be the case, as appropriate, in the course of one and the same in-ladle treatment as a function of the expected result.

It is well known that steel in the ladle can be stirred pneumatically (bubbling) or electromagnetically. When it is pneumatic (the most frequent case in the ladle), stirring is conventionally done by blowing inert gas, usually argon, with the aid of a ladle bottom injector, in general a porous plug.

Schematically, to be effective, the pneumatic stirring of the steel must be of sufficient intensity to fulfill the role assigned to it without however causing overly large eddies at the surface of the bath. If the stirring intensity is too weak, the metallurgical operations might not be completed at the time of casting. Conversely, overly energetic stirring causes excessive agitation of the bath. This may be harmful for example to inclusion cleanliness, since the inclusions arising from the metallurgical operations are then entrained by the eddies and remain in the liquid metal until casting without having time to decant. Moreover, slag may be entrained in the metallic bath in some quantity and pollute the final steel. Furthermore, and especially when not working under vacuum, one runs the risk of reoxidation of the steel by coming directly into contact with the oxygen of the air if the eddies break the continuity of the floating slag layer. In the extreme, uncontrolled agitation may even cause splashes of liquid steel and of slag which foul the device to the point of preventing start-up of the next charge.

Hence, for many years it has been sought to measure the intensity, and thereby, the quality of the stirring carried out so as to optimize it by appropriate adjustments. In the case of the pneumatic stirring at which the invention is directed, this measurement consists most generally in simply tracking the flow rate of gas injected so as, with the aid of pre-established charts, to keep it within the flow rate range desired for the operation in progress in the ladle by acting as required on the inlet valve which controls the pressure.

Unfortunately, the flow rate measurements thus gathered are often not properly representative of the actual agitation of the bath. Multiple factors may falsify these measurements, in particular gas leaks by passage between the metal carcass of the ladle and its refractory cladding, so that the stirring flow rate entering the bath is not known from measuring the flow rate of the gas supply.

When it is possible, a visual inspection of the agitation of the surface of the bath allows a person skilled in the art to empirically assess the quality of the stirring. This eventuality is however rare, and in any event inoperative for moderate stirrings, for example at the end of treatment, on account of the presence of a thick layer of floating slag at that time.

It is known to afford a solution via a "vibratory" approach of the agitated bath. Document U.S. Pat. No. 6,264,716, for example, describes such a procedure of real-time vibratory analysis, the basic principle of which is simple: a bath of liquid matter pneumatically agitated in a ladle necessarily generates vibratory phenomena which carry quantitative information about the stirring if one knows how to exploit it through appropriate processing of the signal received. The analysis of this previously processed vibratory measurement then makes it possible to compare it with a predetermined span of values within which it is considered that the stirring is optimal and the stirring gas supply pressure is adjusted accordingly to ensure, and without necessarily knowing it, the appropriate blowing rate.

In practice, a sensor, of accelerometer type, is placed on the wall of the ladle and will receive the radial vibration of the latter. After conventional filtering, the signals gathered are amplitude-conditioned, digitized-sampled, then evaluated numerically with the aid of a discrete Fourier transform computation. Subsidiarily, the results of this Fourier analysis may be sent in real time to a controller which outside of the occurrence of known nuisance events (momentary additions of powder, temperature taps, additions of alloy elements, etc.), and as a function of presets determined by predefined vibratory thresholds, must make it possible to ensure optimal stirring of the bath for each processing step. Optionally, in order to minimize damage brought about by the temperature of the ladle on the sensor, the latter might not be placed in direct contact with the carcass of the ladle. For this purpose, it is proposed that a movable support piece which is interposed between them be added, or that the sensor be placed on the gas injection system itself or on the connection housing linking the ladle to its frame.

This known system of vibratory analysis is not however entirely satisfactory. Specifically, it has been demonstrated that the signal sensed is polluted by undesirable vibratory components related to particular resonant modes (especially gravitation modes) situated at very low frequencies of the steel bath, or to electrical glitches. Moreover, the user is regularly confronted with problems inherent with spectral computation by discrete Fourier transform. Additionally, this system does not allow the user to have feedback on the state of obstruction of the porous plug or on the gas leaks, if any, in the device.

The invention is thus aimed at proposing another solution for vibratory tracking and real-time control of ladle bubbling by analog and digital filterings of vibratory signals arising from sensors, and also making it possible to detect any leaks or to assess the state of obstruction of the porous plug.

Accordingly, the subject of the invention is a method of vibratory control of the bubbling of a metallic bath in a ladle, or in another similar metallurgical vessel, according to which, a stirring gas being introduced through the bottom of the ladle, the vibration, representative of the vibratory level to be measured, is gathered by at least one sensor placed on the ladle or on its frame, the signals sent being sampled and digitized, characterized in that, prior to their sampling-digitization, said vibratory signals are processed by means of "high-pass" analog filters and in that, after their sampling-digitization, they are subjected to a second filtering, this time digital, calibrated for the vibratory response specific to said ladle, and, after sequencing of the successive digitized signals, each sequence is then subjected to the calculation of a sliding temporal quadratic mean from which is then extracted a global RMS (standing for "Root Mean Square") effective value of the vibratory signal thus measured, which effective value is used to adjust the flow rate of stirring gas delivered to the vessel.

Preferably, the vibratory signals gathered are also processed by "low-pass" analog filtering, doing so in order to avoid the phenomenon known as "aliasing", inherent in the digitizing of the signal, which may contain non-negligible components beyond the Nyquist frequency, equal to half the sampling frequency.

In a preferred implementation of the invention, the digital filters used for the second filtering operation are impulse response IR filters, preferably infinite impulse response filters (IIR filters), which are typically effected through a "recursive" linear operation. The benefit of recursive filters such as these is their small computational cost, their small delay, and their relative stability which may be obtained by adhering to certain precautions of use, especially as regards the ratio between the cutoff frequencies of the IR filter and the sampling frequency.

In a preferred embodiment of the invention, the effective value (or RMS) of the vibratory signal thus measured is transmitted in real time to a system for automatic adjustment of the flow rate of the gas.

The subject of the invention is also a device for the control of the pneumatic stirring of a metal bath in a metallurgical vessel comprising a bottom injector linked to a source of supply of a pressurized stirring gas with the aid of a pipe provided with a pressure-controlled valve for adjusting the flow rate and a flow meter, at least one vibration sensor mounted on the vessel itself or on the frame supporting said vessel, and a unit for processing the vibratory signal gathered by the sensor, the device being characterized in that said signal processing unit comprises at least, and in this successive order, which is that of the processing of the signal: a high-pass analog filter, preferably also a low-pass analog filter, an analog-digital converter, a digital filter calibrated on the vibratory responses of said ladle and a computer for computing a sliding temporal quadratic mean of RMS type.

Preferably, the digital filter is an infinite impulse response IIR filter.

The various essential aspects underlying the invention will be picked up one by one and explained hereinafter, but the invention will first of all be well understood in view of the description of the example which follows, given by way of example with reference to the attached plates of drawings in which.

Figure 1:
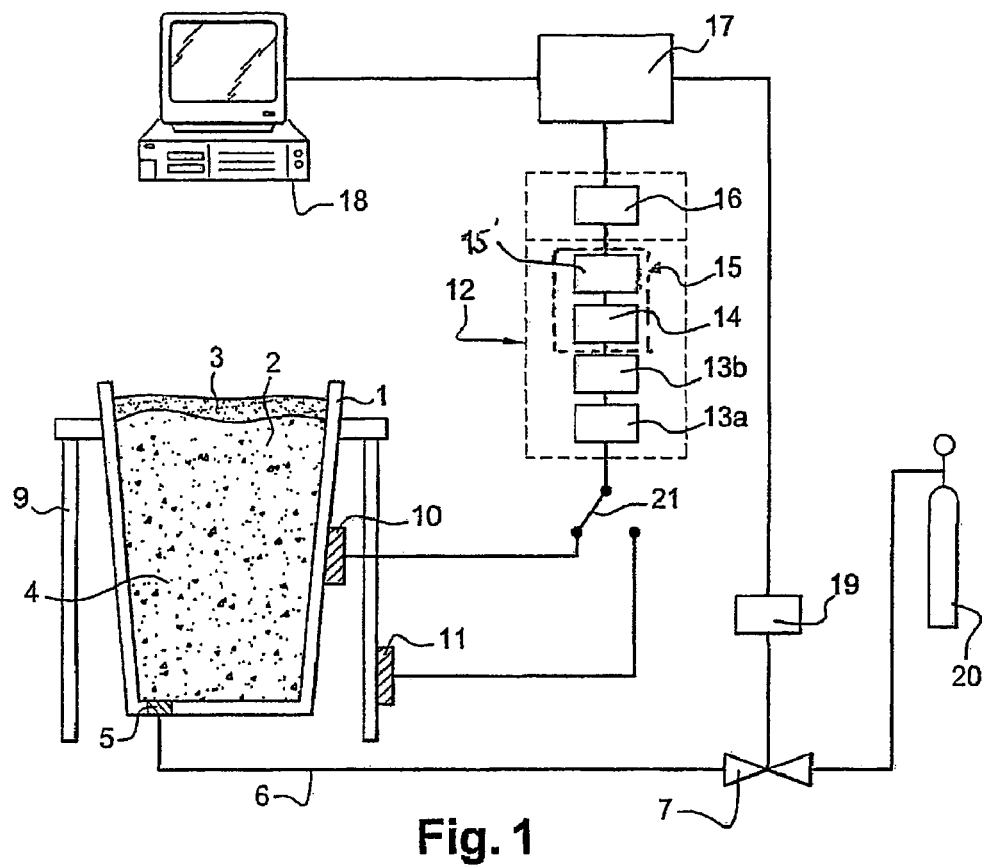
FIG. 1 is a diagram of the device implemented according to the invention.

The method will now be described with reference mainly to FIG. 1 in which is depicted a steelworks ladle 1 containing liquid steel 2 covered with a continuous floating layer of slag 3. The ladle is in place on a support frame 9 with a view to its subsequent transfer to the distributor of the continuous casting device. The liquid metal in the ladle is stirred pneumatically by means of a stream of argon 4 introduced through a bottom porous plug 5.

The stirring gas is brought to the injector 5 from a pressurized source 20 with the aid of a pipe 6 provided with a flow rate adjustment electrovalve 7 conventionally fitted with a pressures sensor and with a flow meter (neither of which are represented).

Figure 2:
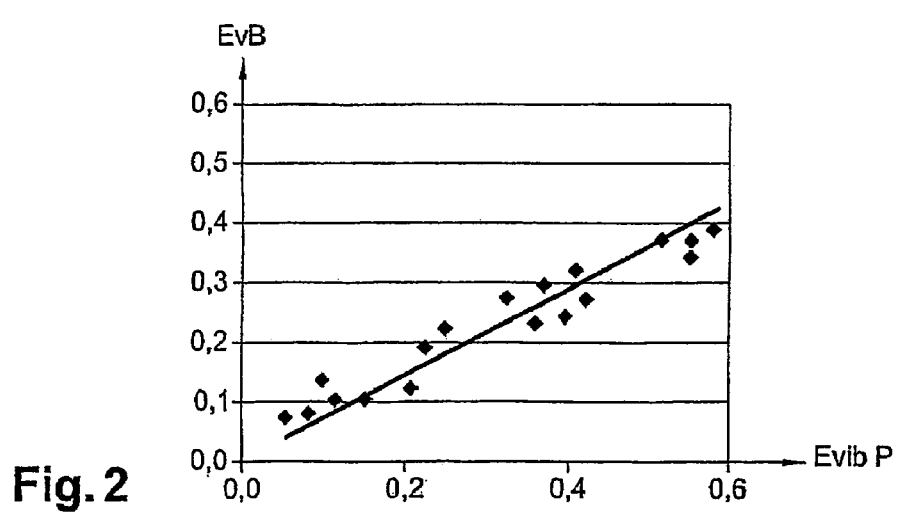
FIG. 2 is a graph representing the correlation between the vibratory energy Evib P measured on the ladle (abscissa) and that Evib B measured on the frame.

The phenomena of vibration of the ladle-metallic bath assembly that are generated by the pneumatic stirring due to the injection of argon are gathered by a vibratory sensor of "accelerometer" type. This sensor 10 may be placed on the ladle 1 in contact with the metal shell directly or via a connection housing 11 provided for this purpose on the support frame 9 ensuring a rigid mechanical link with the ladle at the time of bubbling for example. The invention also enables the sensor to be disposed anywhere on the frame, or on any other stationary element of the device that is linked rigidly to the ladle. In this case, the signal gathered is no longer directly the vibratory signal of the ladle, but that transmitted by the device. Specifically, as may be seen in the graph of FIG. 2, it has been demonstrated that the vibratory energy of the support frame grows linearly as a function of that of the ladle, so that a measurement of the vibration of the frame accounts with great consistency for the vibration of the ladle.

To determine the optimal position of the sensing point or points, the dynamic transfers from the interior of the ladle to the exterior wall or to the existing supports on the bubbling stand are studied beforehand. This study may be done once and for all by spectral analysis of SIMO (Single Input, Multiple Output) or MIMO (Multiple Input, Multiple Output) type in less than a day with an empty ladle. It makes it possible to deduce an optimal position and an optimal direction of inspection of the sensor(s) for the bubbling stand considered. Hence, the vibratory measurement will be made with a maximum of sensitivity and a maximum of consistency with the internal wall loads associated with the actual bubbling.

When one of the positions chosen is situated on the external surface of the ladle, the vibratory measurement is made in the radial direction.

The vibratory sensor 10 is preferably of piezoelectric type. It is placed on the wall of the ladle manually or automatically and is held there by means of a permanent magnet. The external wall of the ladle being able to reach high temperatures, the sensor chosen is therefore preferably devoid of embedded electronics to withstand temperatures of up to 480° C. without particular cooling. Its mechanical sensitivity is high (minimum of 100 pC/g). It is advantageously fitted with differential wiring, which gives it very low electromagnetic sensitivity and exhibits a very low thermal drift. Of course, if one opts for an implanting of the sensor not directly on the ladle itself, the thermal stress at the level of the sensor then being in principle smaller, it will be possible to use sensors of even greater mechanical sensitivity. If the sensor is situated on a stationary element of the device, the support frame in this instance, its position and its orientation are previously established in such a way as to perform optimal vibratory measurement. The sensor used 11 is then of piezoelectric seismic accelerometer type with integrated electronics (ICP). This type of sensor withstands temperatures of the order of 120 to 150° C., and exhibits very high sensitivity: its ICP outputs are of the order of 1000 mV/g for an analysis frequency of 2000 Hz.

The positioning of the sensor on the support frame 9 of the ladle has the advantage of avoiding manipulations for fitting and removing the sensor on the ladle.

Furthermore, it makes it possible to use sensors with higher sensitivity, since they are required to operate at lower temperature. Moreover, the sensors generally being held by means of a permanent magnet, the risks of deficiency of this fastening on account of heat are also reduced.

The vibratory signal thus gathered by the sensor 10 (or 11) is processed in a signal processing unit 12.

A toggle switch 21 may moreover be advantageously provided upstream of the unit 12 for connecting, by choice, to the sensor 10 mounted on the ladle or to the sensor 11 of the frame.

Initially, the signal is preprocessed therein by a high-pass 13a followed by a low-pass 13b analog filter (or vice versa). The high-pass analog filtering 13a makes it possible to eliminate the components at very low frequencies, mentioned above, related to the modes of vibration (gravitation modes) of the metallic mass constituting the bath of steel considered. Moreover it makes it possible to remove the glitches related to the frequency of the electric mains (namely 50 Hz and its first harmonics, in Europe). The low-pass analog filtering 13b makes it possible, for its part, to avoid the well-known phenomena of aliasing inherent in any subsequent digitization of the signals. Stated otherwise, this low-pass filtering 13b, although not indispensable in all strictness for the first implementation of the invention, nevertheless constitutes a "convenience" for the post-digitization processing part, which it would be a pity to do without.

These analog filterings 13a, 13b may be carried out in a very simple manner using passive analog filters configured electronically on the basis of a minimum order. Preferably, an order 8 is advised, thereby making it possible to obtain filter slopes at 48 dB/Octave, given that incrementing the order by a unit value amounts to increasing the slope of the filters by 6 dB on either side of the low and high cutoff frequencies. In this way, the rate of rejection of the undesirable frequency components will be satisfactory.

As far as the choice of the cutoff frequency of the high-pass analog filter is concerned, the latter is made after analysis and expert assessment of the vibration spectra obtained for various bubbling regimes. In particular, bubbling with the highest stirring intensity must make it possible to readily identify, as appropriate, the harmful presence of gravitation modes whose components may, if they are not effectively filtered, completely "swamp" the frequency components associated with the phenomenon of bubbling proper.

The choice of the cutoff frequency of the low-pass analog filter is made, for its part, by following the conventional rules of signal processing relating to the resolution of aliasing problems related, as is known, to the digitizing of signals: before any analog/digital conversion, it should in fact be ensured that the signal to be digitized does not contain frequency components beyond the Nyquist frequency (which is the sampling frequency divided by 2). If, for any reason whatsoever, applying a low-pass analog filtering such as this does not prove to be possible however, care will be taken to perform an over-sampling of the signals so as to ensure that, in the neighborhood of the Nyquist frequency, the spectral components are naturally very weak.

The signals thus filtered are then digitized in the analog/digital converter 15. For this purpose, they are conventionally sampled first of all in a sampling stage 14, then digitized in the digitization stage 15' proper. On account of the "high-pass" analog filtering to which they have previously been subjected, the digitization system 15 can concentrate the whole of the coding dynamics on the useful components of the signal representative of the bubbling phenomenon.

Thereafter, the numerical computation of a sliding temporal quadratic mean, the so-called "sliding RMS mean value" (RMS standing for "Root Mean Square"), is performed with the aid of the computer 17 on the digitized signals previously filtered by one or more digital filters 16. The prior analog pre-filtering 13a, 13b makes it possible to also integrate into the computation of this quadratic mean, "useful" high-frequency components related to the bubbling which otherwise would have been swamped in the background noise of the signal. The spectrum of these components is in fact of the "wideband" type with useful components ranging up to 2000 Hz and even beyond.

The digital filters 16 used are for example IR (impulse response) filters, preferably of IIR (infinite impulse response) type. Their templates (preferably of the "band pass" type) are calibrated as a function of the vibratory responses specific to each type of ladle used. This calibration is carried out, for a given ladle type, after thorough study of conventional vibration spectra obtained for various bubbling regimes. This prior expert assessment makes it possible, on the one hand, to identify and to locate in the frequency domain the zones related to the bubbling phenomenon proper, and, on the other hand, to advocate the filtering template most suited to the extraction of the useful components of these frequency signatures specific to each type of ladle. Various families of template exist in the computational program within the computer, and make it possible to choose, for a given vibratory signature of a type of ladle used, the most appropriate filtering: Butterworth filter, Bessel filter, 0.5 dB Chebyshev filter, 2 dB Chebyshev filter. Other templates may of course also be programmed. Regardless of the choice of the digital filtering, one will preferably opt for the maximum order available in the existing program of the digital filterings, namely the order 10, so as to obtain the "steepest" possible filter slopes. The principal characteristics of these filters are as follows:

Bessel filter: it is characterized by a small "overshoot" in its response to a step ramp. On the other hand, its slope at the cutoff frequencies is small, this having the effect of integrating into the filtered signal, spectral components situated in the neighborhoods of the cutoff frequencies of the band pass filter considered.

Butterworth filter: it is characterized by a very small ripple inside the band of the band pass filter, and by a slope of "medium" steepness at the cutoff frequencies. On the other hand it shows a very big overshoot effect in its response to a step ramp.

Chebyshev filter: it is characterized by very big slopes at the cutoff frequencies, and may be parameterized in terms of ripple ratio in the band of the band pass filter considered. The existing program makes it possible to define this ripple ratio at a value of 0.5 dB or 2 dB.

These digital filterings are followed by the computation proper, and in real time, of a sliding temporal quadratic mean of the RMS type over a time span of duration T that is fully parameterizable by the user (as a multiple N of the original sampling interval $\Delta t$: $T=N.\Delta t$). This computation is then repeated for a new time slice of N samples, which is obtained by temporal translation of the previous time slice: the value of this temporal translation is parameterizable, but, it is preferably chosen equal to the sampling interval $\Delta t$. This procedure is then continued for all the subsequent time slices, until the end of the in-ladle bubbling treatment. One thus obtains an RMS mean for all the sampling intervals Δt, and each time computed for a time slice of duration T=N.Δt, thereby ultimately delivering a sliding RMS mean value K(t) of the vibratory level as a function of time. A typical value of N is 4000 time samples, for a sampling frequency fe of 4000 Hz, i.e. Δt=1/fe hence T=1 sec.

The computation of this RMS mean quadratic value is carried out practically by summing, for a given time slice of N samples (that is to say over a time N.Δt), the squares of all the values of the N time samples of the previously filtered vibratory signal, then by dividing the result of this sum by the number N of samples, so as to obtain a mean value of the vibratory energy in the time slice considered. Finally, the square root of this energy mean is computed, thereby providing a quantity dimensionally equivalent to an effective signal value, called the RMS value (Root Mean Square, or Mean Quadratic Value) for the time slice considered and for the frequency bands defined by the various analog and digital filterings. This computed mean quadratic value, denoted K hereinafter, of the vibratory level may be used as a simple and effective indicator of the quality of the in-ladle bubbling. It is in fact accepted that the vibration of the ladle is amplified correlatively with the increase in the flow rate of argon injected into the steel.

Figure 3:
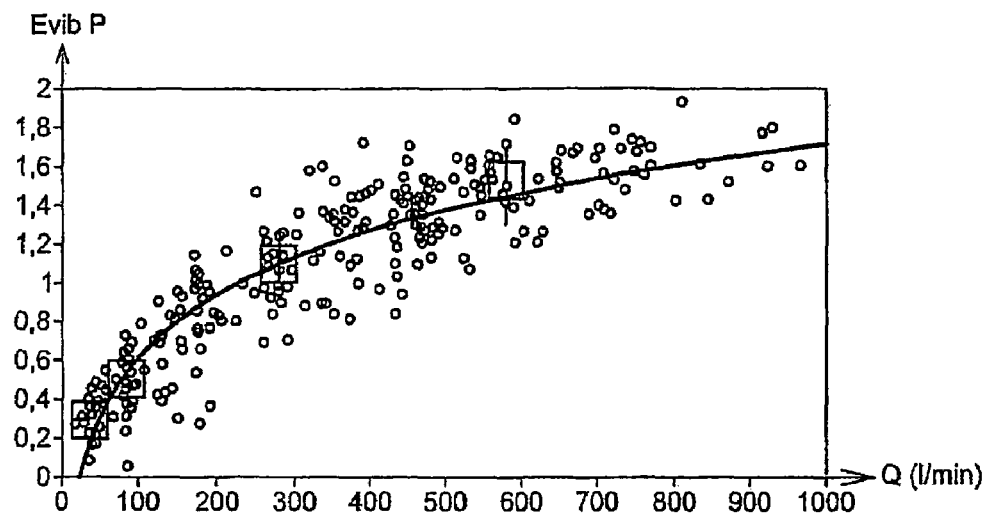
FIG. 3 is a graph representing the vibratory energy Evib P of the ladle (ordinate) as a function of the flow rate Q of stirring argon injected.

Going further still, it has been demonstrated that this amplification occurs according to a mean curve of logarithmic type, as shown by FIG. 3. It has also been proven that the only obvious factors influencing the vibratory signal, other than the actual flow rate of argon, are the state of the porous plug and leaks. It has also been established during trials that the quantity and the rheology of the slag have no influence on the vibratory signal, no more than the size of the ladle or the composition of the grade.

Figure 4:
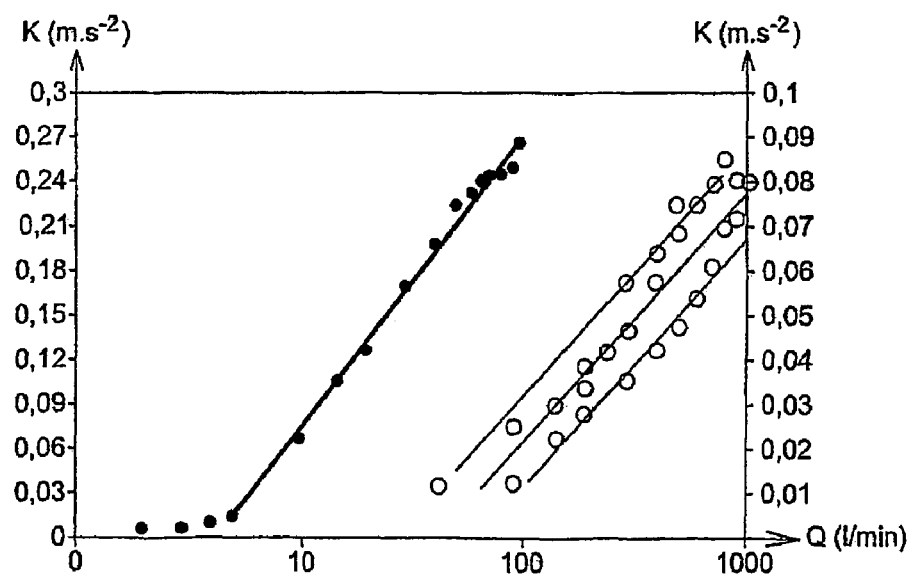
FIG. 4 is a double graph correlating the bubbling indicator K (ordinate) as a function of the flow rate Q of stirring argon injected placed as abscissa on a logarithmic scale.

Specifically, the mean quadratic value K of the vibratory energy computed follows a law according to which K=A Log($Q_{gas}$)+B, $Q_{gas}$ being the quantity of gas injected into the steel. The graph of FIG. 4 clearly illustrates the foregoing. The gas flow rate Q is plotted as abscissa on a logarithmic scale and K is given as ordinate, according to two examples side by side.

a) the left part represents laboratory trials on a mockup with water (the molten steel is replaced with water)
 b) the right part represents industrial trials performed on a 90-tonne steelworks ladle.

In the laboratory (left part) the measurement points unfurl according to a quasi-perfect straight line in the flow rate bracket involved. Only the very flat toe is witness to the fact that the very small initial flow rates (less than 8 l/min) have no real influence on the vibratory state of the ladle.

In the factory (right part), the measurement points unfurl in essence also according to a very pure straight line (shown bold in the figure). A certain scatter is observed on either side, which however remains confined within a quite rectilinear band 0.02 units wide. This is witness to inevitable disturbances in an industrial environment, but which do not in any way impair the reliability of the procedure.

By means of this first simple indicator of bubbling, it is possible to establish a second indicator which provides evidence of the state of obstruction of the porous plug. To do this, the signals delivered by the pressure governor and the flow meter (neither of which are represented) of the supply valve 7 for the porous plug 5 are gathered so as to have a figure indicative of the flow rate of argon theoretically injected into the ladle. This acquisition is done jointly with the measurement of the vibratory signal of the ladle by the sensor 10 (or 11). With the aid of an operator desk 18, these various data are then transmitted to the computer 17 (which incorporates a database of production specific to the workshop considered—the in-ladle treatment station in this instance) so as to be analyzed there and thus allow real-time detection of a gas leak or the partial obstruction of the porous plug. The computer can advantageously be linked to a system 19 for automated control of the flow rate of argon by adjustment of the degree of opening of the flow valve 7, so as to alter the stirring gas stream.

During trails carried out on site, this system has made it possible to detect a leak or poor operation of the porous plug for three out of nine castings at a low flow rate at the end of treatment, not visible solely by flow rate/pressure tracking.

Moreover, the use of more sensitive sensors makes it possible to lower the bubbling detection threshold down to a real flow rate of argon of less than 40 l/min. Hence, it is now possible to program at the conclusion of the working of the steel a stirring that is gentle enough to assist the decantation of the inclusions in the covering slag without particles of said slag being entrained in the bath.

Thus on sheet metal of conventional ferritic grade for example, the control of the in-ladle bubbling according to the invention has made it possible to reduce the rate of formation of oxidized lines through the programming of a gentle bubbling at the conclusion of the in-ladle treatment. It had in fact been established previously that these defects resulted from the trapping in the steel of inclusions as well as ladle slag.

The invention finds its preferred application in the field of a bubbling of metal at the stand of a steelworks ladle. However, as already indicated, it remains applicable in a general manner to any measurement of the vibratory energy of a metallurgical vessel containing pneumatically stirred liquid metal, such as converters or steelworks arc furnaces for example, or RH vessels.

It goes without saying that the invention may not be limited to the example described, but that it extends to multiple variants or equivalents in so far as the definition thereof given in the adjoining claims is complied with.

The invention claimed is:

1. A method of vibratory control of bubbling of a metallic bath in a ladle, or in another similar metallurgical vessel, the method comprising:
 stirring the metallic bath by a stirring gas introduced through a porous plug of the ladle or vessel;
 gathering vibration signals, representative of a vibratory level to be measured, by at least one sensor placed on the ladle or vessel or on a frame of the ladle or vessel;
 processing the vibration signals by high-pass analog filters to remove frequencies associated with gravitation modes of the metallic mass to concentrate the whole of coding dynamics on useful components of the vibration signals representative of a bubbling phenomenon;
 sampling-digitizing the vibration signals by a digitizer, and, after the sampling-digitizing, filtering the vibration signals by a digital filter calibrated for vibratory responses specific to the ladle or vessel;
 sequencing successive digitized signals, and after the sequencing, subjecting each sequence to calculation of a sliding temporal quadratic mean from which is then extracted a global RMS effective value of the vibration signal thus measured, which effective value is used to adjust a flow rate of the stirring gas delivered to the ladle or vessel;
 analyzing a theoretical flow rate of the stirring gas from measurements of at least one of a pressure governor and a flow meter of the porous plug; and comparing a result of the analyzing with the effective value to determine a leak or obstruction of the porous plug.

2. The method as claimed in claim 1, wherein the vibration signals gathered are also processed by low-pass analog filtering.

3. The method as claimed in claim 1, wherein infinite impulse response IIR filters are used to carry out the filtering by the digital filter.

4. The method as claimed in claim 1, wherein the temporal quadratic mean of the vibration signals is transmitted to a system of automated control of flow rate of the stirring gas.

5. The method as claimed in claim 1, wherein the metallurgical vessel is a steelworks ladle.

6. The method as claimed in claim 1, wherein the at least one sensor is placed on a frame of the ladle.

7. The method as claimed in claim 1 further comprising, before the stirring of the gas introduced through the bottom of the ladle or vessel, determining a position for placement of the at least one sensor based on spectral analysis of the ladle or vessel.

8. The method according to claim 7, wherein the spectral analysis is performed with an empty ladle or empty vessel.

* * * * *